United States Patent [19]

Murakami

[11] Patent Number: 5,597,703

[45] Date of Patent: Jan. 28, 1997

[54] METHOD FOR DETERMINING CHOLESTEROL OXIDASE

[75] Inventor: Toru Murakami, Tokyo, Japan

[73] Assignee: NEC Corporation, Tokyo, Japan

[21] Appl. No.: 401,227

[22] Filed: Mar. 9, 1995

[30] Foreign Application Priority Data

Mar. 10, 1994 [JP] Japan ................................ 6-039707
Apr. 21, 1994 [JP] Japan ................................ 6-083269

[51] Int. Cl.⁶ .............................. C12Q 1/26; C12Q 1/60
[52] U.S. Cl. .............................. 435/25; 435/11; 436/172
[58] Field of Search .............................. 435/11.25, 808, 435/968, 969; 436/71, 172

[56] References Cited

U.S. PATENT DOCUMENTS 4,195,126  3/1980  Hall .......................................... 435/11

FOREIGN PATENT DOCUMENTS 574358  4/1986  Japan .

OTHER PUBLICATIONS

Slotte, J. P., Effect of Sterol Side–Chain Structure on Sterol–Phosphatidylcholine Interactions in Monolayers and Small Unilamellar Vesicles, Biochimica et Biphysica Acta 1190 Mar. 1994 435–443.

Mattjus, P., Monolayer Interaction of Cholesterol with Phosphatidylcholines: Effects of Phospholipid Acyl Chain Length, Chemistry and Physics of Lipids, 74 Dec. 1994, 195–203.

Methods of Enzymatic Anaysis, vol. 1, Fundamentals, 3rd Edition, 1983, pp. 210–217.

*Primary Examiner*—Ralph Gitomer
*Attorney, Agent, or Firm*—Sughrue, Mion, Zinn, Macpeak & Seas

[57] ABSTRACT

The invention provides a method for measuring the activity of cholesterol oxidase. First, a monolayer including sterol, a phospholipid and fluorescent dye labeled phospholipid is formed on a surface of a cholesterol oxidase aqueous solution. Then, it is observed whether sterol domain fade-out occurs in the monolayer. The activity of the cholesterol oxidase can be determined on the basis of both the period of time during which the sterol domain fade-out has occurred and a concentration of sterol in a cholesterol oxidase aqueous solution. This process can be applied to a method for estimating the toxicity of chemical compounds.

3 Claims, 5 Drawing Sheets

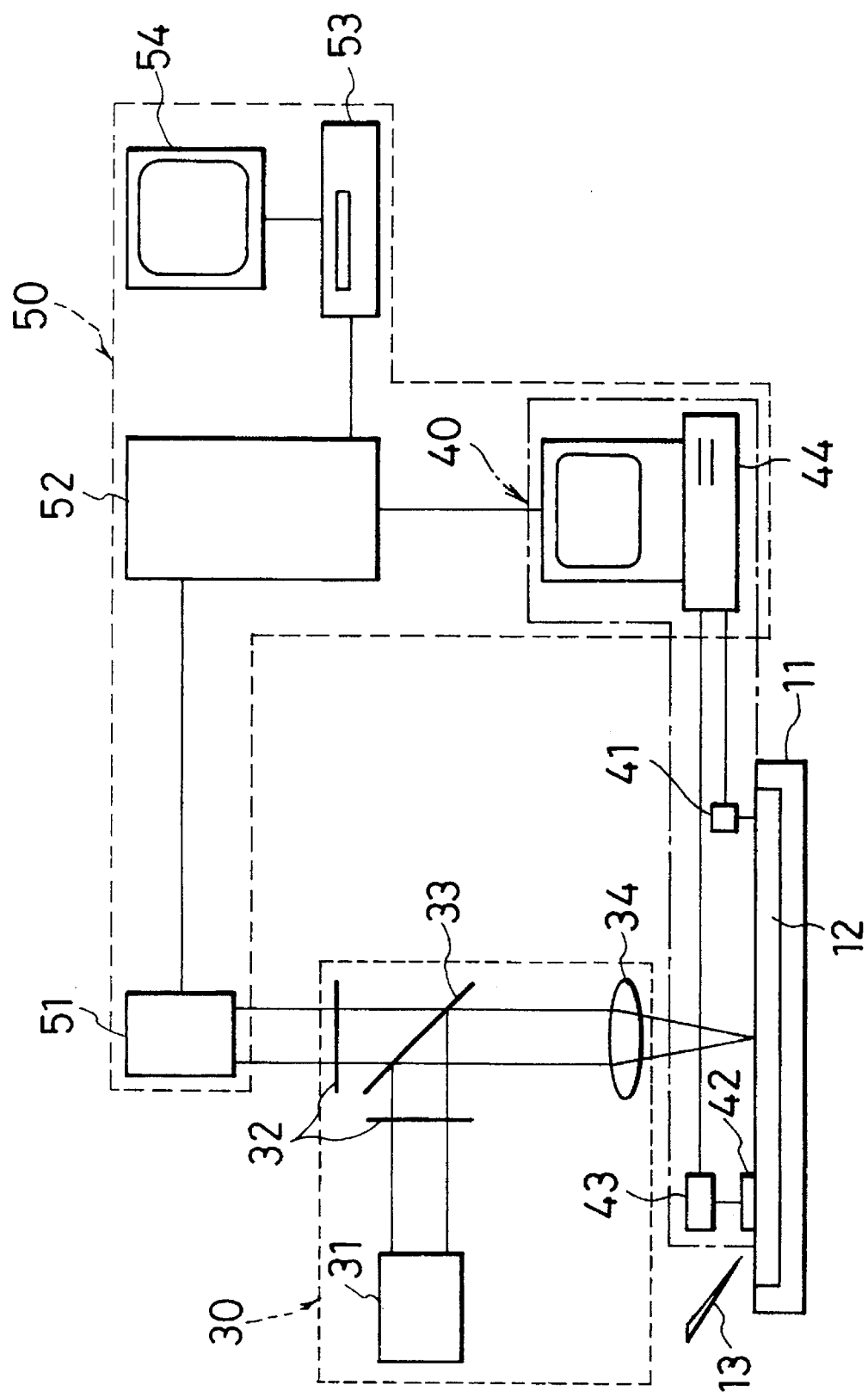

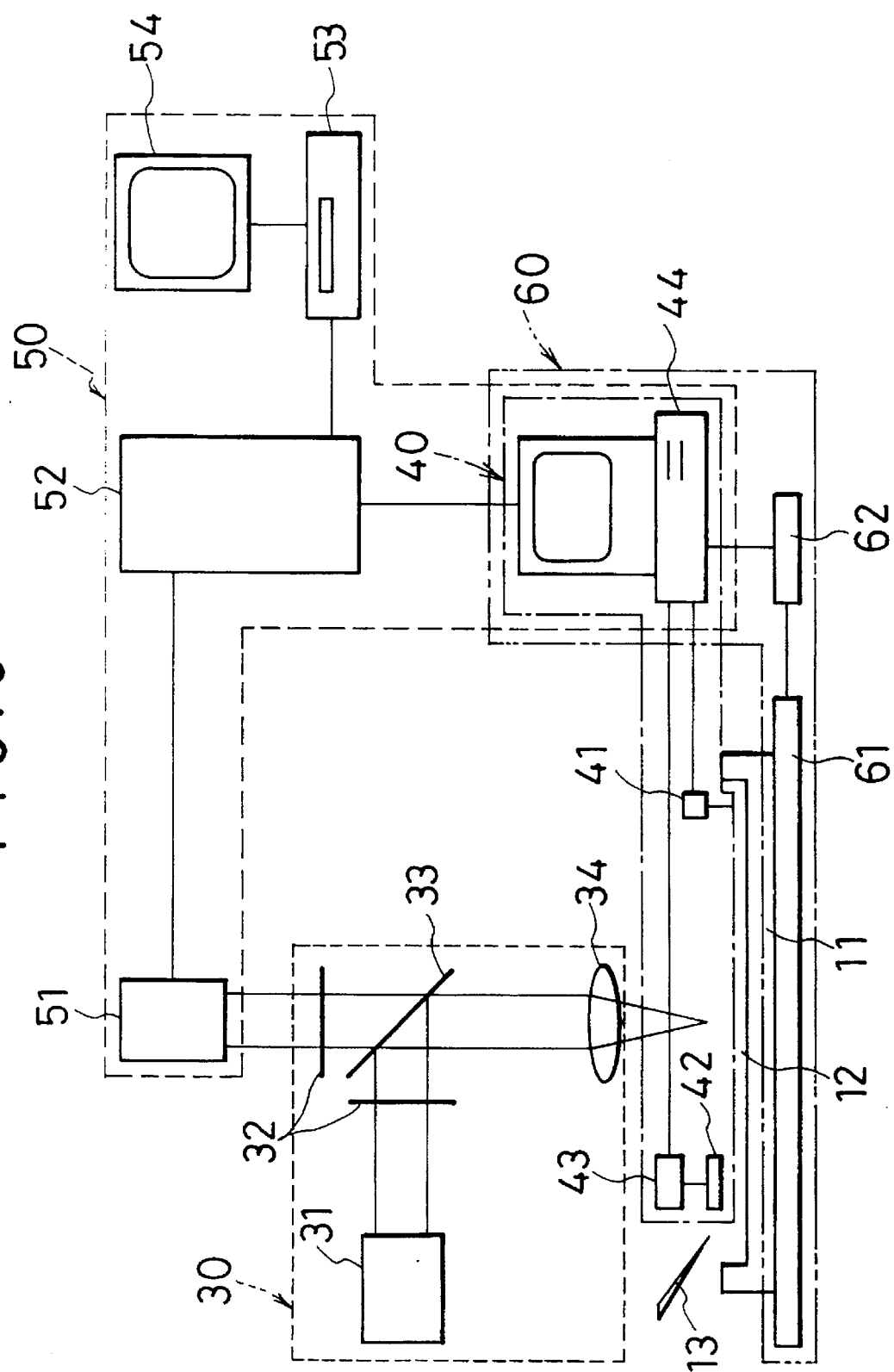

METHOD FOR DETERMINING CHOLESTEROL OXIDASE

BACKGROUND OF THE INVENTION

1. Field of the Invention

The invention relates to a method for measuring the activity of cholesterol oxidase and an apparatus therefor, and also to a method for estimating the toxicity of chemical compounds and an apparatus therefor, and more particularly to such methods and apparatuses utilizing monolayers at the air-water interface.

2. Description of the Related Art

A prior method for measuring the activity of cholesterol oxidase is known as a method for biochemical analysis of cholesterol oxidase, utilized in a quantitative reaction of cholesterol which is one item of clinical examinations. Hereinbelow will be explained several prior methods for measuring the activity of cholesterol oxidase.

The first method is one reported in Methods of enzymatic analysis, Vol. 1, Fundamentals, 3rd edition, 1983. As shown in an equation (A), cholesterol is oxidized in the presence of cholesterol oxidase working as a catalyst, to thereby produce cholestenone and hydrogen peroxide ($H_2O_2$).

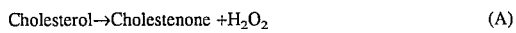

$$\text{Cholesterol} \rightarrow \text{Cholestenone} + H_2O_2 \quad (A)$$

This method measures the activity of cholesterol oxidase by directly measuring hydrogen peroxide produced in accordance with the equation (A) with an ultraviolet (UV) ray.

In the second method, methanol is first oxidized to formaldehyde with $H_2O_2$ produced in accordance with the equation (A) and catalase as a catalyst. Then, the thus produced formaldehyde is reacted with acetylacetone and ammonia, and thus there is produced 3,5-diacetyl-1,4-dihydrolutidine. In this second method, the degree of activity of cholesterol oxidase can be measured by measuring the absorbance of 3,5-diacetyl-1,4-dihydrolutidine at the wavelength in the range from 405 nm to 415 nm.

In the third method, hydrogen peroxide ($H_2O_2$) produced in accordance with the equation (A) is reacted with phenol and 4-aminoantipyrine in the presence of peroxidase. Then, a dye produced by such a reaction measured at the wavelength of 515 nm by means of absorptiometry to thereby measure the activity of cholesterol oxidase.

In the fourth method, hydrogen peroxide ($H_2O_2$) produced in accordance with the equation (A) is reacted with MBTH (3-methyl-2-benzothiazolinone hydrazone) and dimethylaniline in the presence peroxidase. Then, a dye produced by such a reaction is measured at the wavelength of 600 nm by means of absorptiometry to thereby measure the activity of cholesterol oxidase.

In the fifth method, hydrogen peroxide ($H_2O_2$) produced in accordance with the equation (A) is reacted with ABTS (2,2'-azino-di-[3-ethylbenzthiazolinesulphonic acid]) in the presence of peroxidase. Then, a cation radical produced by such a reaction is measured at the wavelength in the range from 420 nm to 436 nm to thereby measure the activity of cholesterol oxidase.

In the sixth method, luminol is oxidized by hydrogen peroxide ($H_2O_2$) produced in accordance with the equation (A) in the presence of peroxidase. Then, the chemical luminescence energy generated in such oxidization is measured to thereby measure the activity of cholesterol oxidase.

It is illegal to directly test human beings to analyze the toxic effects of chemical compounds on the human body. Hence, conventional methods for estimating the toxicity of chemical compounds use mammals other than a human being, such as animal cells and micro-organisms, to test medicines, food additives, industrial wastes, organism producing products and so on as to whether they have general toxicity, such as acute toxicity, short term toxicity and long term toxicity, particular toxicity such as mutagen, partial stimulus, allergy, tumogenicity, teratogenicity and propagation, and residence in a human body concerning respiration, metabolism, accumulation and excretion. Furthermore, general biological estimates such as pharmacological estimates with respect to cell toxicity are made to thereby predict the toxicity of chemical compounds toward a human being. For instance, Japanese Patent Publication No. 5-74358, which is based on U.S. patent application Ser. No. 623,183, published on Oct. 18, 1994 in Japan has disclosed a method for determining the cell toxicity. In this method, while cells are being cultured, fluorescent substances and a drug are introduced to the cells. By analyzing the change of fluorescence in the cells, the sensitivity of the cells to the drug is measured.

Cholesterol is not soluble in water. Accordingly, in all conventional methods for measuring the activity of cholesterol oxidase, substrate cholesterol is dispersed in water by using a surfactant and then the activity of cholesterol oxidase is measured. However, the thus obtained enzymatic activity is not one between cholesterol and cholesterol oxidase, but one representing the interaction among cholesterol, surfactant and cholesterol oxidase. Accordingly, the activity of cholesterol oxidase is varied in dependence on a surfactant used. In addition, the above mentioned prior method in which a surfactant, enzyme and a dye have to be used requires complex handling for measurement.

The conventional methods for estimating the toxicity of chemical compounds mainly use an animal other than a human being and a cell for conducting a test. In the case of using an animal other than a human being as an object to be tested, it is required to spend a lot of cost, time and labor for breeding animals and for estimating the toxicity. Furthermore, an animal test is not preferable in view of the prevention of cruelty to animals. In the case of using cells, much time and labor is required for culturing cells, and it takes a lot of time to determine the estimate of toxicity because the handling for the estimate is quite complicated.

SUMMARY OF THE INVENTION

In view of the above mentioned problems of the conventional methods, it is an object of the present invention to provide a method by which the activity of cholesterol oxidase between cholesterol and cholesterol oxidase can easily be measured without using a surfactant.

Another object of the present invention is to provide a method by which the estimate of the toxicity of chemical compounds can easily and rapidly be carried out without using an animal and cells as an object to be tested.

In one aspect, the invention provides a method for measuring the activity of cholesterol oxidase, including the steps of (a) forming a monolayer on a surface of a cholesterol oxidase aqueous solution, where the monolayer includes sterol and phospholipid and fluorescent dye labeled phospholipid, (b) observing sterol domain fade-out occurring in the monolayer with a fluorescence microscope, and (c) determining the activity of the cholesterol oxidase on the basis of both the period of time during which the sterol domain fade-out has occurred and a concentration of sterol in the cholesterol oxidase aqueous solution.

In another aspect, the invention provides an apparatus for carrying out the above mentioned method. The apparatus includes (a) a surface pressure balance for measuring a surface pressure of the monolayer, (b) a barrier having a width equal to a width of a trough in which the cholesterol oxidase aqueous solution is contained, the barrier floating on a surface of the cholesterol oxidase aqueous solution in the trough and movable in the length-wise direction of the trough, (c) a driver for moving the barrier to thereby vary a surface area of a region in which the monolayer is to be formed, and (d) a controller for controlling the driver in accordance with the surface pressure of the monolayer measured by the surface pressure balance.

In still another aspect, the invention provides a method for estimating the toxicity of chemical compound, including the steps of (a) dissolving or dispersing a chemical compound to be tested in cholesterol oxidase aqueous solution, (b) forming a monolayer on a surface of the cholesterol oxidase aqueous solution, the monolayer includes sterol and phospholipid and fluorescent dye labeled phospholipid, (c) observing sterol domain fade-out occurring in the monolayer with a fluorescence microscope, and (d) estimating the toxicity of the chemical compound in accordance with the presence or absence of the sterol domain fade-out.

In yet another aspect, the invention provides an apparatus for carrying out the above mentioned method. The apparatus includes (a) a surface pressure balance for measuring a surface pressure of the monolayer, (b) a barrier having a width equal to a width of a trough in which the cholesterol oxidase aqueous solution is contained, floating on a surface of the cholesterol oxidase aqueous solution in the trough, ,and movable in the length-wise direction of the trough, (c) a driver for moving the barrier to thereby vary a surface area of a region in which the monolayer is to be formed, and (d) a controller for controlling the driver in accordance with the surface pressure of the monolayer measured by said surface pressure balance.

In a preferred embodiment of both of the above mentioned apparatuses, the apparatus further includes (a) a television camera for taking pictures of the sterol domain fade-out occurring in the monolayer, (b) an image processor for analyzing the pictures, (c) a recorder for recording the pictures, (d) a monitor camera for displaying the pictures, and (e) a controller for controlling the television camera, image processor, recorder and monitor camera.

In another preferred embodiment of both of the above mentioned apparatuses, the apparatus further includes (a) a X-Y stage for disposing the trough thereon, and (b) a controller for controlling the X-Y stage.

In still another preferred embodiment of both of the above mentioned apparatuses, the trough is a circular-shaped trough having a plurality of radially divided sections.

In yet another preferred embodiment of both of the above mentioned apparatuses, the apparatus further includes (a) a rotatable stage for disposing the circular-shaped trough thereon, and (b) a controller for controlling both rotation speed and rotation angle of the rotatable stage.

The advantages obtained by the aforementioned present invention will be described hereinbelow.

In the method and apparatus for measuring the degree of activity of cholesterol oxidase in accordance with the invention, on a surface of cholesterol oxidase aqueous solution is formed a monolayer composed of sterol, phospholipid and fluorescent dye labeled phospholipid. Hence, it is no necessary to use a surfactant, which was necessary in the conventional methods. Accordingly, a surfactant does not affect the degree of activity of cholesterol oxidase, and hence it is possible to obtain correct data regarding the interaction between cholesterol and cholesterol oxidase. In addition, the handling of the present method is easier than the conventional methods.

In the method and apparatus for estimating the toxicity of chemical compounds in accordance with the invention, on a surface of cholesterol oxidase aqueous solution, in which is dissolved a chemical compound in which the toxicity thereof is to be estimated, is formed a monolayer composed of sterol, phospholipid and fluorescent dye labeled phospholipid, and then the observation is carried out with a fluorescence microscope as to whether sterol domain fade-out occurs or not in the monolayer to thereby estimate the toxicity of the chemical compound. It is no longer necessary to culture cells, and hence it is possible to determine visibility and quickly whether the chemical compound has toxicity or not. In addition, since an animal is not used as an object to be experimented, it is possible to reduce the cost of the experiment and also prevent cruelty to animals.

The above and other objects and advantageous features of the present invention will be made apparent from the following description made with reference to the accompanying drawings, in which like reference characters designate the same or similar parts throughout the drawings.

BRIEF DESCRIPTION OF THE DRAWINGS

FIG. 4 is a schematic view illustrating an apparatus both for measuring the activity of cholesterol oxidase and for estimating the toxicity of chemical compounds, in accordance with the second embodiment of the invention.

FIG. 5 is a schematic view illustrating an apparatus both for measuring the activity of cholesterol oxidase and for estimating the toxicity of chemical compounds, in accordance with the third embodiment of the invention.

DESCRIPTION OF THE PREFERRED EMBODIMENTS

Preferred embodiments in accordance with the present invention will be explained hereinbelow with reference to drawings.

Figure 1A:
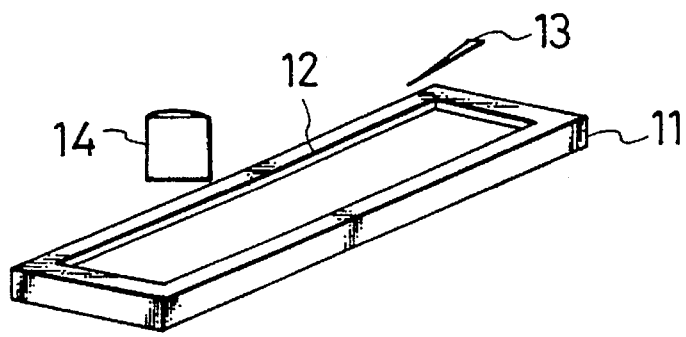
FIG. 1A is a perspective view of an apparatus for forming a monolayer.
Figure 1B:
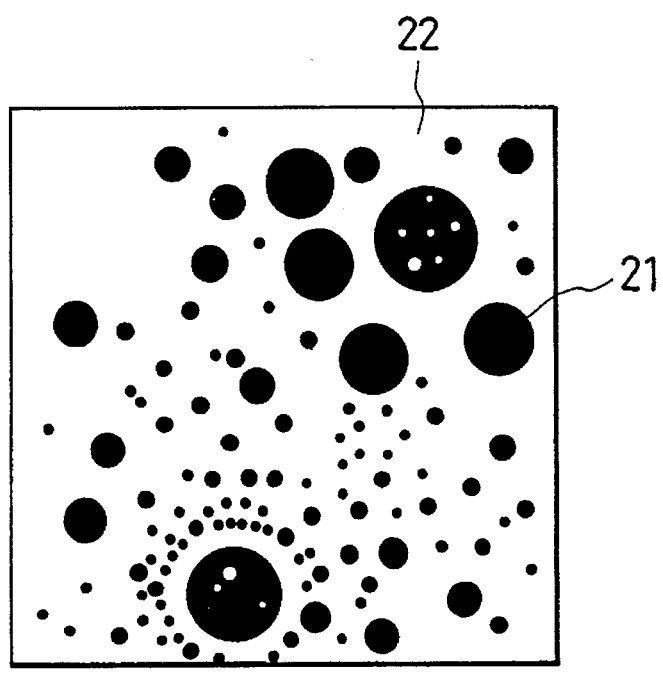
FIG. 1B is a schematic view of a picture of a monolayer taken with a fluorescence microscope just after monolayer formation.
Figure 1C:
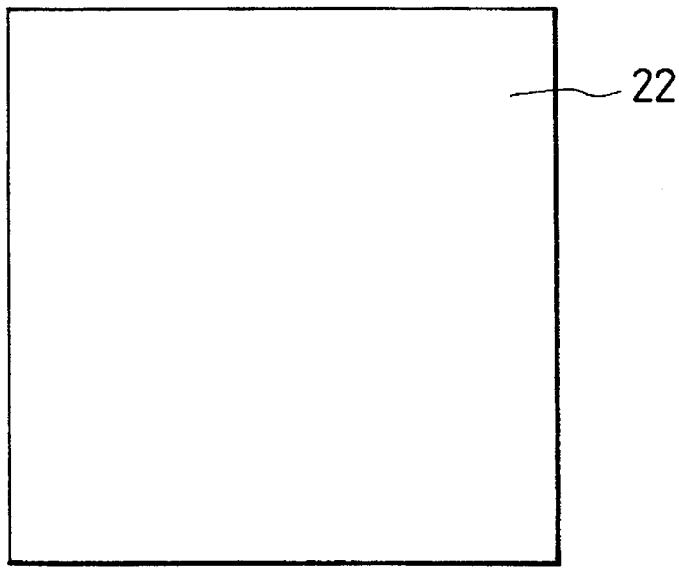
FIG. 1C is a schematic view of a picture of a monolayer when a certain period of time has passed after a monolayer was formed.

FIG. 1A illustrates an apparatus for forming and also observing a monolayer. In a rectangular-shaped trough 11 is filled cholesterol oxidase aqueous solution 12. Onto a surface of the cholesterol oxidase aqueous solution 12 is dropped monolayer spread solution 13 to thereby form a monolayer. Microscopic pictures of the monolayer such as shown in FIGS. 1B and 1C are obtained by observing the monolayer with a fluorescence microscope through an objective 14. Dark (black) regions in FIG. 1B indicate sterol domain 21, while bright (white) regions indicate phospholipid 22. The coexisting two phases are observed in FIG. 1B, namely both the dark sterol domain 21 and the bright phospholipid 22 are present. In FIG. 1C, the dark sterol domain 21 has vanished, and only the bright phospholipid 22 is observed.

Hereinbelow is explained an embodiment of the method for measuring the degree of activity of cholesterol oxidase in accordance with the invention. In the embodiment, there are used cholesterol oxidase HEPES buffer solution of $2\times10^{-3}$ unit/ml and $5\times10^{-3}$ unit/ml as the cholesterol oxidase aqueous solution 12. Herein, HEPES means N-2-hydroxyethylpiperazine-N'-2-ethane sulfonic acid which has 0.1 of ionic strength and 7.45 of pH. There are also used spread solutions #1–#5 as the monolayer spread solution 13, each of the solutions being composed of DMPC (L-α-dimyristoylphosphatidylcholine), cholesterol and fluorescent dye labeled phospholipid NBD-PC (1-palmitoyl-2-[12[-(7-nitro-2-1,3-benzoxadiazol-4-yl)amino]dodecanoyl]phosphatidylcholine) chloroform, and having different component ratio as shown in Table 1.

TABLE 1

| | Monolayer Spread Solution | | |
|---|---|---|---|
| | DMPC/mM | Cholesterol/ml | NBD-PC/mM |
| #1 | 0.58 | 0.4 | 0.02 |
| #2 | 0.68 | 0.3 | 0.02 |
| #3 | 0.78 | 0.2 | 0.02 |
| #4 | 0.88 | 0.1 | 0.02 |
| #5 | 0.93 | 0.05 | 0.02 |

For instance, if the monolayer spread solution #2 is dropped in the amount of 9.4 ml thereof onto a surface (42.6 cm$^2$) of the cholesterol oxidase aqueous solution 12 of $2\times10^{-3}$ unit/ml, there is immediately formed a monolayer on the surface. Then, the thus formed monolayer is observed with a fluorescence microscope by using 450–490 nm exaltation filter and a cut filter which cuts wavelengths shorter than 520 nm, and thereby there is obtained a microscopic picture as illustrated in FIG. 1B, showing coexisting two phases in which both the dark sterol domain 21 and the bright phospholipid (DMPC+NBD-PC) 22 are present. The sterol domain 21 gradually vanishes as times go by, and in approximately 30 minutes all of the sterol domain 21 is no longer visibly observable as illustrated in FIG. 1C. As shown in Table 2, a period of time for fade-out of the sterol domain is dependent both on the sterol concentration in the monolayer spread solution 13 and the activity of cholesterol oxidase. Accordingly, it is possible to determine the activity of cholesterol oxidase by dropping a monolayer spread solution including sterol at the known concentration onto a surface of cholesterol oxidase aqueous solution 12 of which the activity is unknown, to thereby form a monolayer on a surface of the cholesterol oxidase aqueous solution 12, and further by measuring a period of time taken for fade-out of the sterol domain 21 per a certain surface area.

TABLE 2

| | Period of Time for Fade-out of Sterol Domain [min] | | | | |
|---|---|---|---|---|---|
| Cholesterol oxidase/unit/ml | #1 | #2 | #3 | #4 | #5 |
| $2\times10^{-3}$ | 35 | 30 | 26 | 20 | 14 |
| $5\times10^{-3}$ | 18 | 16 | 14 | 13 | 8 |

Hereinbelow will be explained four embodiments of the method for estimating the toxicity of chemical compounds in accordance with the invention with reference to FIGS. 1A, 1B and 1C.

In the first embodiment of the method for estimating the toxicity of chemical compounds, there is used cholesterol oxidase HEPES buffer solution of $5\times10^{-3}$ unit/ml as the cholesterol oxidase aqueous solution 12. Herein, HEPES means N-2-hydroxyethylpiperazine-N'-2-ethane sulfonic acid which has 0.1 of ionic strength and 7.45 of pH. In the HEPES solution is dissolved 1 mM of zinc chloride the toxicity of which is to be estimated. As the monolayer spread solution 13, there is used a solution consisting of 0.68 mM of DMPC (L-α-dimyristoylphosphatidylcholine), 0.3 mM of cholesterol and 0.02 mM of fluorescent dye labeled phospholipid NBD-PC (1-palmitoyl-2-[12-[(7-nitro-2-1,3-benzoxadiazol-4-yl) amino]dodecanoyl]phosphatidylcholine) chloroform. The monolayer spread solution 13 is dropped in the amount of 9.4 ml thereof onto a surface (42.6 cm$^2$) of the cholesterol oxidase aqueous solution 12 in which 1 mM of zinc chloride is dissolved, and then there is immediately formed a monolayer on the surface. Then, the thus formed monolayer is observed with a fluorescence microscope, and thus there is obtained a microscopic picture as illustrated in FIG. 1B. Even if 30 minutes has passed after monolayer formation, there can be observed a picture as illustrated in FIG. 1B, in which the sterol domain 21 and the phospholipid 22 coexist. This means that zinc chloride is toxic to cholesterol oxidase and thus reduce the activity of cholesterol oxidase.

In the second embodiment, there is used cholesterol oxidase HEPES buffer solution of $5\times10^{-3}$ unit/ml as the cholesterol oxidase aqueous solution 12. In the HEPES solution is dissolved 1 mM of calcium chloride the toxicity of which is to be estimated. As the monolayer spread solution 13, there is used a solution consisting of 0.68 mM of DMPC (L-α-dimyristoylphosphatidylcholine), 0.3 mM of cholesterol and 0.02 mM of fluorescent dye labeled phospholipid NBD-PC (1-palmitoyl-2-[12-[(7-nitro-2-1,3-benzoxadiazol-4-yl)amino]dodecanoyl]phosphatyzircoline) chloroform. Similarly to the first embodiment, the monolayer spread solution 13 is dropped onto a surface of the cholesterol oxidase aqueous solution 12, and then there is immediately formed a monolayer on the surface. Then, the thus formed monolayer is observed with a fluorescence microscope, and thus there is obtained a microscopic picture as illustrated in FIG. 1B. The sterol domain 21 gradually vanishes, and when 30 minutes has passed after the monolayer is cast, a fluorescent microscopic picture as illustrated in FIG. 1C can be observed. It can be concluded that the presence of 1 mM of calcium chloride does not affect the fade-out of the sterol domain, and hence calcium chloride is not toxic to cholesterol oxidase.

In the third embodiment, there is used cholesterol oxidase HEPES buffer solution of $5\times10^{-3}$ unit/ml as the cholesterol oxidase aqueous solution 12. In the HEPES solution is dissolved 1 mM of mercury (II) chloride the toxicity of which is to be estimated. As the monolayer spread solution 13, there is used a solution consisting of 0.68 mM of DPPC (L-α-dipalmitoylphosphatidylcholine), 0.3 mM of dihydrocholesterol and 0.02 mM of fluorescent dye labeled phospholipid NBD-PE (1-palmitoyl-2-[12-[(7-nitro-2-1,3-benzoxadiazol-4-yl) amino]dodecanoyl] phosphatidylethanolamine) chloroform. Similarly to the first embodiment, there is formed a monolayer on a surface of the cholesterol oxidase aqueous solution 12 by dropping the monolayer spread solution 13 as above mentioned on the surface. Then, the thus formed monolayer is observed with a fluorescence microscope, and thus there is obtained a microscopic picture as illustrated in FIG. 1B. The fluorescent microscopic picture obtained when 30 minutes has passed after monolayer formation remains unchanged. Thus, it can be concluded that the presence of 1 mM of mercury (II) chloride suppresses the fade-out of the sterol domain, and hence mercury (II) chloride has the toxicity to cholesterol oxidase.

In the fourth embodiment, there is used cholesterol oxidase HEPES buffer solution of $5 \times 10^{-3}$ unit/ml as the cholesterol oxidase aqueous solution 12. In the HEPES solution is dissolved 0.1 mM of SDS (sodium dodecyl sulfate) the toxicity of which is to be estimated. As the monolayer spread solution 13, there is used a solution consisting of 0.68 mM of DPPE (L-α-tdipalmitoylphosphatidylethanolamine), 0.3 mM of pregnenolone and 0.02 mM of fluorescent dye labeled phospholipid TR-DPPE (N-(texasredsulfonyl)-L-α-dipalmitoylphosphatidylethanolamine) chloroform. Similarly to the first embodiment, there is formed a monolayer on a surface of the cholesterol oxidase aqueous solution 12 by dropping the monolayer spread solution 13 as above mentioned to the surface. Then, the thus formed monolayer is observed with a fluorescence microscope, and thus there is obtained a microscopic picture as illustrated in FIG. 1B. The fluorescent microscopic picture as illustrated in FIG. 1B can be observed both just after monolayer formation and when 30 minutes has passed. Thus, it can be known that 0.1 mM of SDS renders cholesterol oxidase deactivated and thus suppress the fade-out of sterol domain with the conclusion that SDS has the toxicity to cholesterol oxidase.

As shown in the above mentioned four embodiments, it is possible to estimate the toxicity of chemical compounds easily and visibly by dissolving or dispersing chemical compounds the toxicity of which is to be estimated in the cholesterol oxidase aqueous solution 12, and further by observing the presence or absence of the fade-out of sterol domain with a fluorescence microscope. It should be noted that there is no limitation in a combination of phospholipid, sterol and fluorescent dye labeled phospholipid which constitute the monolayer spread solution 13 used in the embodiments, and also in a combination of chemical compounds the toxicity of which is to be estimated and the monolayer spread solution 13.

Figure 2:
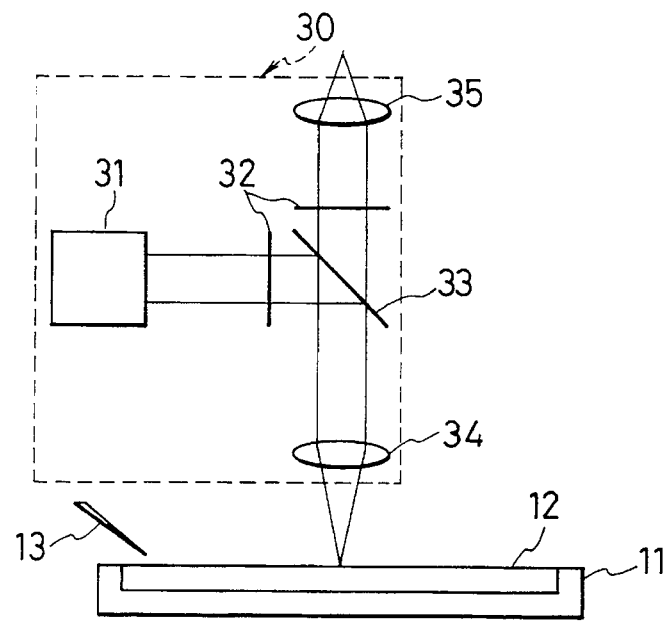
FIG. 2 is a schematic view illustrating an apparatus to be used in the methods for measuring the activity of cholesterol oxidase and for estimating the toxicity of chemical compounds.

With reference to FIG. 2, herein below will be explained an apparatus for carrying out the methods for measuring the activity of cholesterol oxidase and for estimating the toxicity of chemical compounds. The apparatus has a fluorescence microscope 30 and a trough 11. The fluorescence microscope 30 includes a light source 31, an optical filter 32 through which light beam transmitted from the light source 31 passes, a dichroic mirror 33 for dividing the light into two beams, an objective 34 through which one of the divided beams passes, and an eye-piece 35 through which the other of the divided beams passes. The trough 11 contains either the cholesterol oxidase aqueous solution 12 when the method for measuring the activity of cholesterol oxidase is to be carried out, or the cholesterol oxidase aqueous solution 12 containing therein chemical compounds the toxicity of which is to be estimated when the method for estimating the toxicity of chemical compounds is to be carried out.

First, onto a surface of the cholesterol oxidase aqueous solution 12 in the trough 11 is dropped the monolayer spread solution 13 to thereby form a monolayer on the surface. Then, the thus formed monolayer is observed with the fluorescence microscope 30. As aforementioned in the four embodiments, the activity of cholesterol oxidase is measured in view of the speed of the observed fade-out of sterol domain and the sterol concentration in the monolayer spread solution 13, and the toxicity of chemical compounds is estimated in accordance with the presence or absence of the sterol domain fade-out.

Figure 3A:
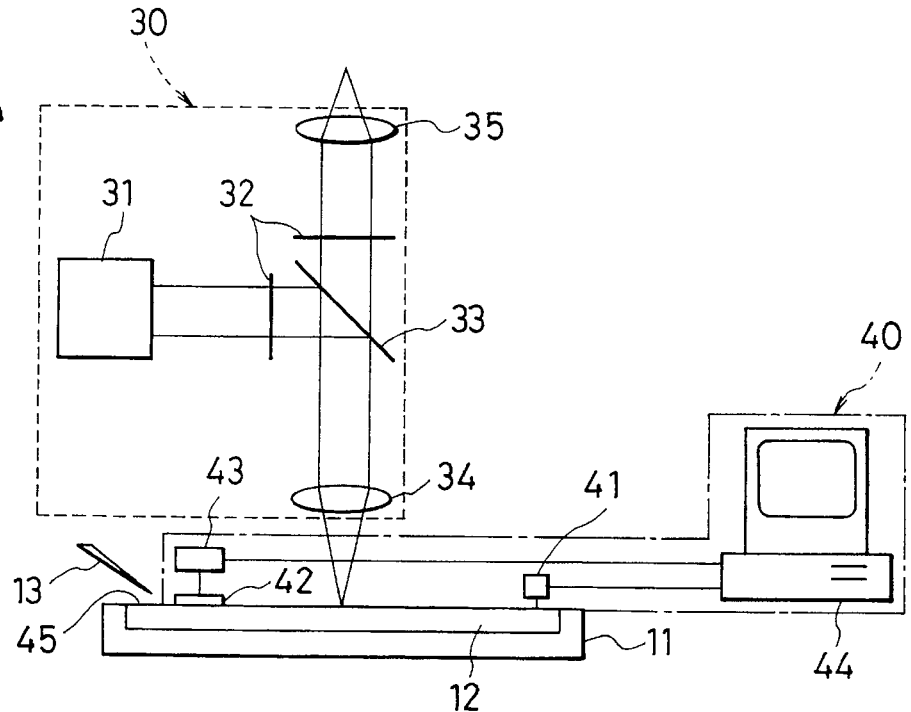
FIG. 3A is a schematic view illustrating an apparatus both for measuring the activity of cholesterol oxidase and for estimating the toxicity of chemical compounds, in accordance with the first embodiment of the invention.
Figure 3B:
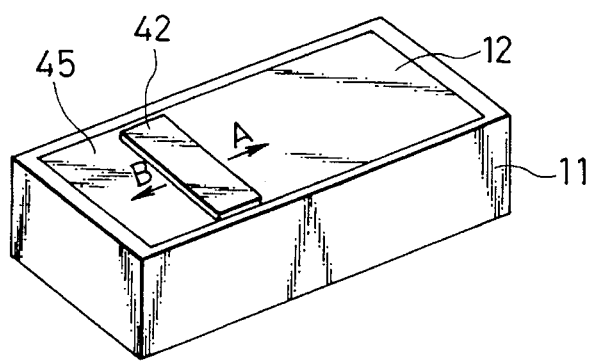
FIG. 3B is a partial top perspective view of the apparatus illustrated in FIG. 3A.

FIGS. 3A and 3B illustrate an apparatus for measuring the activity of cholesterol oxidase and estimating the toxicity of chemical compounds. Comparing to the apparatus illustrated in FIG. 2, the apparatus illustrated in FIGS. 3A and 3B further includes a surface pressure controlling device 40. The device 40 includes a surface pressure balance 41 for measuring a surface pressure of the monolayer 12, a barrier 42 floating on a surface of the cholesterol oxidase aqueous solution 12, a driver 43 for moving the barrier 42 along the surface of the cholesterol oxidase aqueous solution 12, and a controller 44 for controlling the driver 43 in accordance with the surface pressure of the monolayer 12 measured by the surface pressure balance 41.

As illustrated in FIG. 3B, the barrier 42 has a width equal to a width of the trough 11 containing the cholesterol oxidase aqueous solution 12 therein, and is designed to be movable in the length-wise direction of the trough 11, namely the direction indicated by arrows A and B. As the barrier 42 is driven to move by the driver 43, a surface area of a region 45 onto which the monolayer spread solution 13 is dropped to thereby form the monolayer is varied. Specifically, when the barrier 42 is driven to move in the direction indicated by the arrow A, a surface area of the region 45 is increased, while when the barrier 42 is driven to move in the direction indicated by the arrow B, a surface area of the region 45 is decreased.

During the observation of the fade-out of sterol domain with the fluorescence microscope 30, the surface pressure balance 41 measures a surface pressure of the monolayer. The surface pressure balance 41 transmits a signal representing the measured surface pressure to the controller 44. The controller 44 transmits a signal to the driver 43 so that the driver 43 moves the barrier 42 in the direction indicated by either the arrow A or the arrow B, to thereby vary a surface area of the monolayer. Accordingly, it is possible to keep the surface pressure of the monolayer to be constant. Thus, it is possible to keep a film pressure of the monolayer to be identical in each of the measurements, and hence a measurement or estimate with high accuracy can be carried out.

FIG. 4 illustrates the second embodiment of an apparatus for measuring the activity of cholesterol oxidase and for estimating the toxicity of chemical compounds. Comparing to the apparatus in accordance with the first embodiment as illustrated in FIG. 3A, the apparatus in accordance with the second embodiment additionally includes an image processing apparatus 50. The image processing apparatus 50 includes a television camera 51 for taking pictures of the sterol domain fade-out occurring in a monolayer, an image processor 52 for analyzing said pictures, a video-recorder 53 for recording the pictures, a monitor camera 54 for displaying the pictures, and a controller 44 for controlling the television camera 51, the image processor 52, the recorder 53 and the monitor camera 54.

By observing the sterol domain fade-out with a fluorescence microscope not through naked eyes but through the television camera 51 it is possible to continuously observe and record the sterol domain fade-out. In addition, the image processor 52 can carry out various processing to the observed pictures, such as background subtraction, averaging, contrast enhancement, and so on. Hence, it is possible to measure a period of time taken for the sterol domain fade-out, and whether the sterol domain fade-out has occurred or not with high accuracy and further in detail.

FIG. 5 illustrates the third embodiment of an apparatus for measuring the activity of cholesterol oxidase and for estimating the toxicity of chemical compounds. Comparing to the apparatus in accordance with the second embodiment as illustrated in FIG. 4, the apparatus in accordance with the third embodiment additionally includes a X-Y stage apparatus 60. The apparatus 60 includes a X-Y stage 61 for disposing the trough 11 thereon, a X-Y stage controller 62 for controlling the X-Y stage 61, and the controller 44 for controlling the X-Y stage controller 62 in relation to the image processing apparatus 50 and the surface pressure controlling device 40. The trough 11 is laid on the X-Y stage 61. The X-Y stage controller 62 moves the X-Y stage 61 in X-axis and/or Y-axis direction, and thus it is possible to observe the sterol domain fade-out continuously in a whole region of the monolayer.

Figure 6:
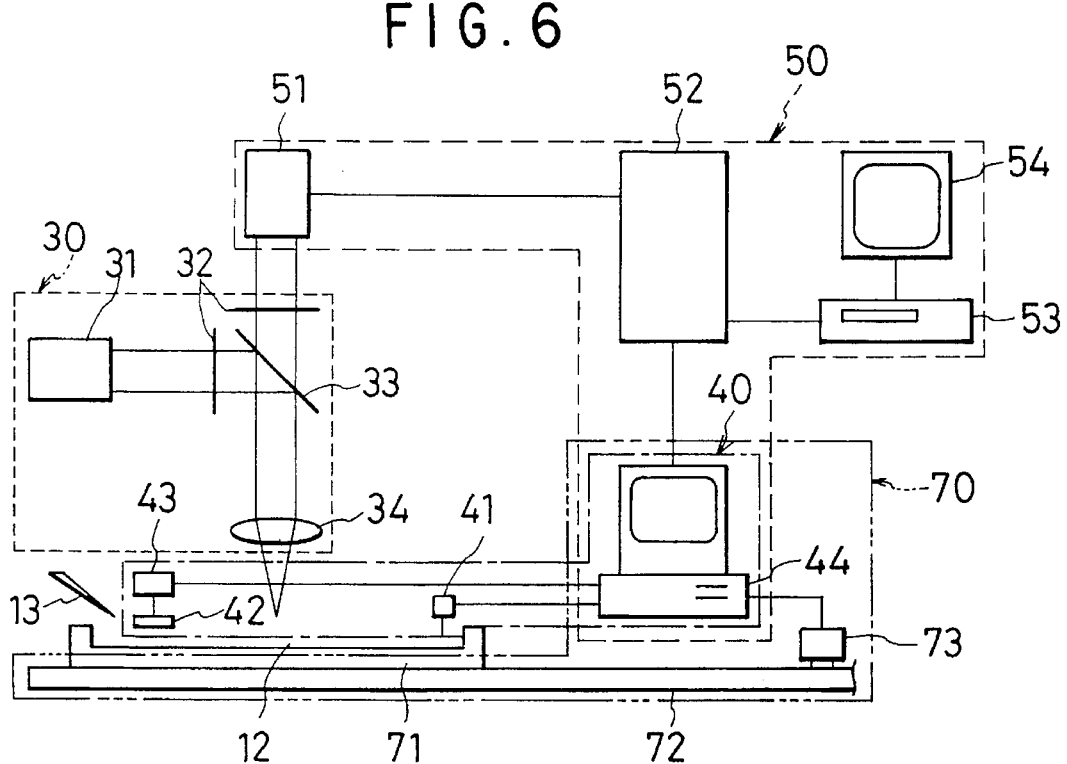
FIG. 6 is a schematic view illustrating an apparatus both for measuring the activity of cholesterol oxidase and for estimating the toxicity of chemical compounds, in accordance with the fourth embodiment of the invention.
Figure 7:
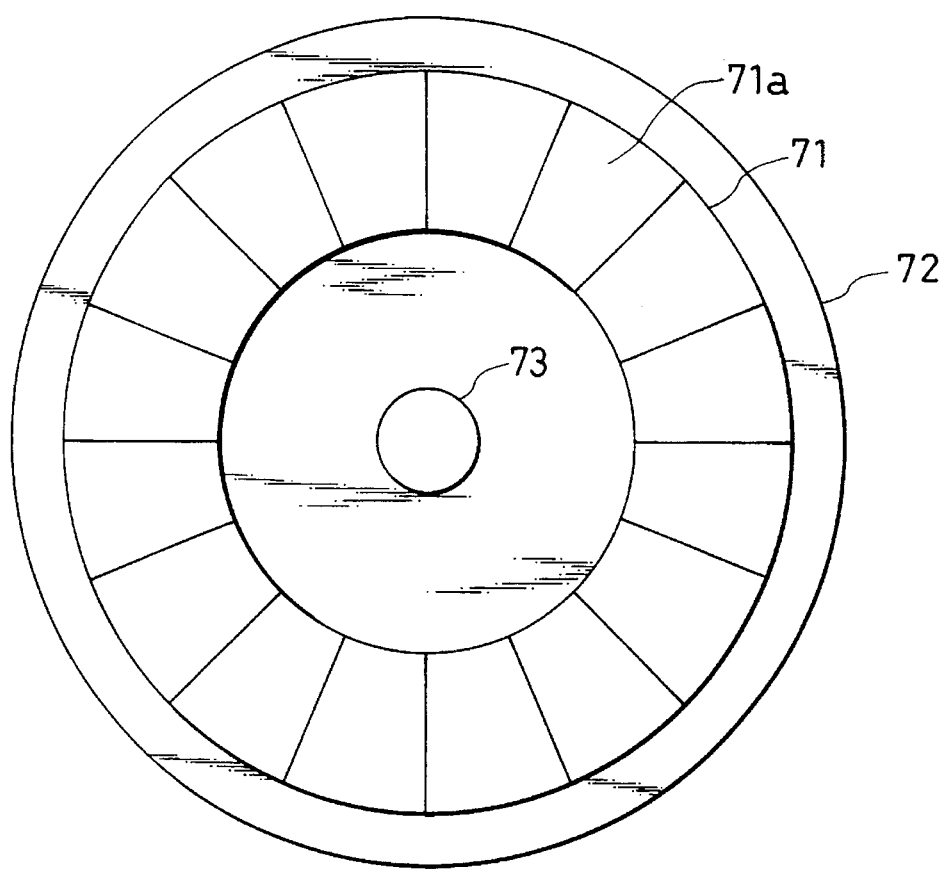
FIG. 7 is a top view of a circular-shaped trough to be used in the apparatus illustrated in FIG. 6.

FIG. 6 illustrates the fourth embodiment of an apparatus for measuring the activity of cholesterol oxidase and for estimating the toxicity of chemical compounds. Comparing to the apparatus in accordance with the third embodiment as illustrated in FIG. 5, the apparatus in accordance with the fourth embodiment uses a circular-shaped trough apparatus 70 in place of the rectangular-shaped trough 11 and the X-Y stage 60. As illustrated in FIG. 7, the circular-shaped trough apparatus 70 includes a circular-shaped trough 71 having a plurality of radially divided sections 71a, a rotatable stage 72 for disposing the circular-shaped trough 71 thereon, and a circular-shaped stage controller 73 for controlling both rotation speed and rotation angle of the rotatable stage 72. In each of the radially divided sections 71a of the circular-shaped trough 71 is filled with cholesterol oxidase aqueous solution each containing a different chemical compound the toxicity of which is to be estimated. The controller 73 rotates the stage 72 on which the circular-shaped trough 71 is disposed, by a predetermined angle so that each of the sections 71a is successively disposed below the monolayer spread solution dispenser 13. Onto a surface of the cholesterol oxidase aqueous solution contained in each of the sections 71a is dropped in order the monolayer spread solution 13 to thereby form a monolayer. After a certain period of time has passed, the fluorescence microscope 30 and the image processing apparatus 50 analyze whether the sterol domain fade-out has occurred or not in the monolayer in the sections 71a, and thereby it is possible to estimate in a short period of time the toxicity of various chemical compounds contained in the sections 71a.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method for determining a cholesterol oxidase activity in an aqueous test sample comprising cholesterol oxidase, comprising the steps of:

(A) forming a monolayer on a surface of said aqueous test sample, wherein said monolayer consists essentially of a pre-determined concentration of sterol, and a phospholipid and fluorescent dye labeled phospholipid;

(B) measuring a period of time during which sterol domain fade-out occurs in said monolayer, as observed with a fluorescence microscope; and (C) determining said cholesterol oxidase activity in said aqueous test sample by comparing said period of time measured in step (B) to the periods of time during which sterol domain fade-out occur on a standard curve obtained using a range of cholesterol oxidase activities and said pre-determined concentration of sterol.

2. A method for determining whether a test compound is capable of inhibiting cholesterol oxidase activity, comprising the steps of:

(A) dissolving or dispersing said test compound in an aqueous solution comprising cholesterol oxidase and having cholesterol oxidase activity;

(B) forming a monolayer on a surface of said aqueous solution, wherein said monolayer consists essentially of sterol, a phospholipid and fluorescent dye labeled phospholipid;

(C) determining whether sterol domain fade-out occurs in said monolayer, as observed with a fluorescence microscope, wherein an absence of said sterol domain fade-out indicates that said test compound inhibits cholesterol oxidase activity.

3. A method for determining a degree of cholesterol oxidase inhibitory activity of a test compound, comprising the steps of:

(A) dissolving or dispersing said test compound in an aqueous solution comprising cholesterol oxidase and having cholesterol oxidase activity;

(B) forming a monolayer on a surface of said aqueous solution, wherein said monolayer consists essentially of sterol, a phospholipid and fluorescent dye labeled phospholipid;

(C) measuring a period of time during which sterol domain fade-out occurs in said monolayer, as observed with a fluorescence microscope;

(D) comparing the period of time measured in step (C) with the period of time during which sterol domain fade-out occurs in said monolayer using said aqueous solution in an absence of said test compound, wherein the difference between said periods of time corresponds to the degree of cholesterol oxidase inhibitory activity of said test compound.

* * * * *

UNITED STATES PATENT AND TRADEMARK OFFICE
CERTIFICATE OF CORRECTION

PATENT NO. : 5,597,703
DATED : January 28, 1997
INVENTOR(S) : Toru MURAKAMI

It is certified that error appears in the above-indentified patent and that said Letters Patent is hereby corrected as shown below:

On the title page, item [54], and column 1, title should read:

--METHODS FOR MEASURING ACTIVITY OF CHOLESTEROL OXIDASE--.

Column 3, line 18, after "solution" insert --where--.

Column 7, line 24, delete "α-tdipalmitoylphosphatidylethanolamine" and insert -- α-dipalmitoylphosphatidylethanolamine--.

Signed and Sealed this

Seventh Day of October, 1997

Attest:

BRUCE LEHMAN

Attesting Officer

Commissioner of Patents and Trademarks